May 1, 1973 D. L. ARMSTRONG Plant Pat. 3,323
ROSE PLANT
Filed April 16, 1971
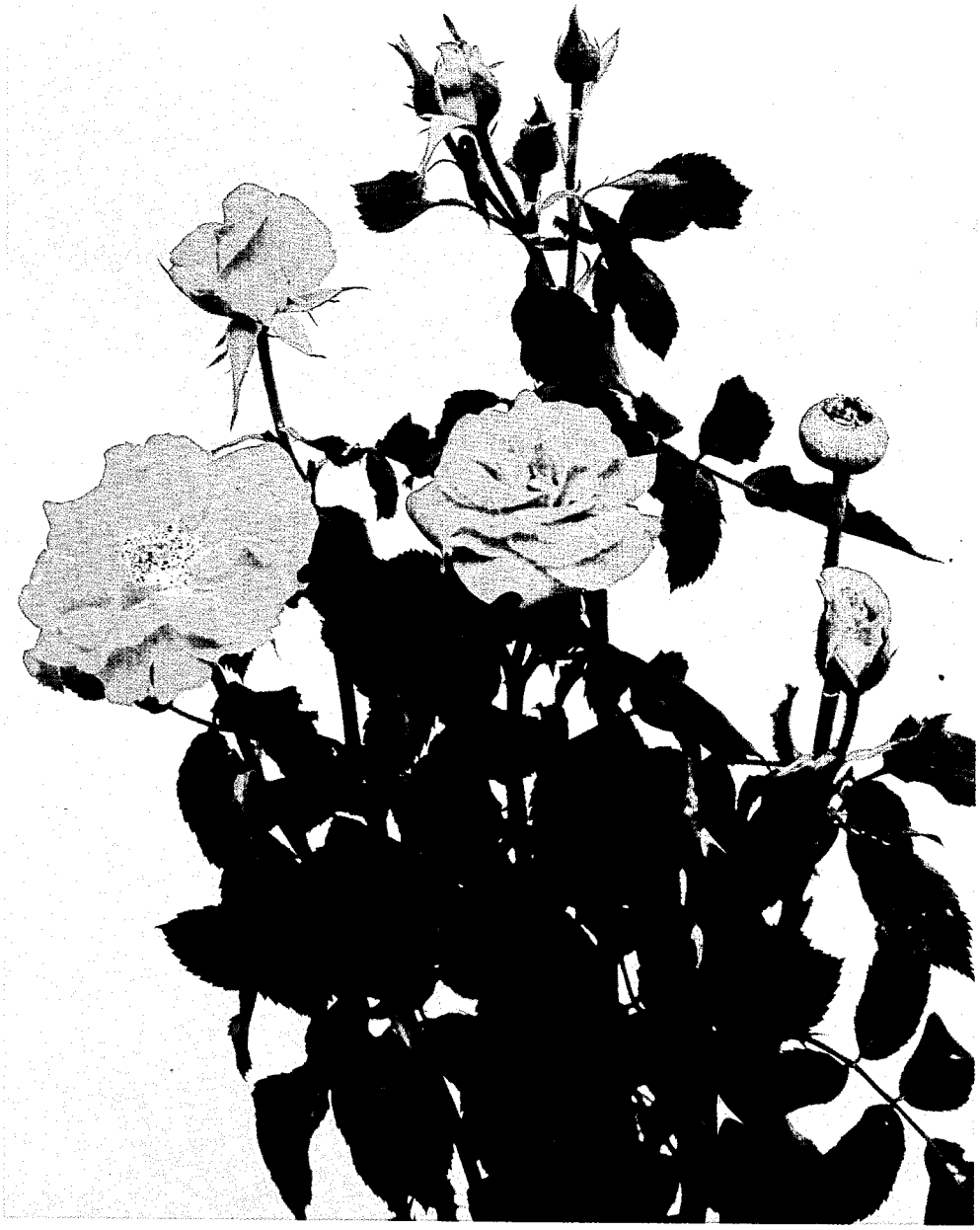

United States Patent Office

Plant Pat. 3,323
Patented May 1, 1973

3,323
ROSE PLANT
David L. Armstrong, Upland, Calif., assignor to
Armstrong Nurseries, Inc., Ontario, Calif.
Filed Apr. 16, 1971, Ser. No. 134,911
Int. Cl. A01h 5/00
U.S. Cl. Plt.—28 1 Claim

ABSTRACT OF THE DISCLOSURE

A rose plant of the fluoribunda class which bears small bright red blooms on normal strength, medium length stems. Sometimes the flowers are borne singly, though usually there are from three to several to a stem in an irregular cluster. The flowers are about 2½ to 2¾ inches across when fully opened, having about 15 or 20 petals. The plant blooms abundantly outdoors almost continuously during the growing season. The general color effect of the newly-opened flowers is strong red.

This invention relates to a new variety of rose plant of the floribunda class. The plant is a seedling of the outdoor bush type, culviated for cut flowers and garden decoration. It was propagated by David L. Armstrong in Ontario, Calif., having as its seed parent "Pink Parfait" (Patent No. 1,904) and, as its pollen parent, "Garnette." It holds its distinguishing characteristics through succeeding propagations by budding.

The new variety usually bears its flowers from three to several on normal strength, medium length stems, in an irregular cluster. Sometimes, however, the flowers are borne singly. The plant blooms abundantly outdoors, and almost continuously during the growing season. It has a slight fragrance.

Differences between this new variety of rose plant and its seed parent, Pink Parfait, includes the following:

The mature plant of this new variety is characteristically spreading, with its flowers borne generally in an upright position; in contrast, the mature plant of Pink Parfait is upright-spreading in form and substantially more upright than the new variety.

The peduncle of the new variety has a great many short, stiff stipitate glands, while the peduncle of Pink Parfait carries a smaller number of stipitate glands, which are much less husky in appearance. On the pericarp of this new cultivar there is an abundance of short, white, stiff hairs, these being almost totally lacking on the pericarp of the Pink Parfait flowers.

The flowers of this new variety are birght red, whereas the flowers of Pink Parfait are pink. The flowers of this new cultivar are substantially smaller than those of Pink Parfait, averaging from about 2½ inches to about 2¾ inches across, whereas the flowers of Pink Parfait run from 3½ inches to 4½ inches in diameter. Furthermore, the flowers of this new variety comprise, on the average, about five petals fewer than the flowers of Pink Parfait.

Differences between this new variety of rose plant and its pollen parent, Garnette, include the following:

Whereas the pericarp of this new variety is typically found with a covering of short, stiff, white hair, such a covering is not found on the pericarps of Garnette flowers, to any significant extent.

The flowers of this new variety are characterized by a petal complement of about fifteen or twenty, whereas the flowers of Garnette may have as many as fifty petals.

The apex of the outer and intermediate petals of this new cultivar are often pointed or acute, whereas the apex of none of the petals in Garnette are other than rounded.

The flowers of this new cultivar are substantially larger, namely about 2½ inches to 2¾ inches in diameter, as compared to the two-inch flowers of Garnette.

The flowers of this new cultivar are typically lighter and brighter red than those of its parent, Garnette.

The plants of this new cultivar become much larger than do those of Garnette, and the flower producing stems are much longer.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

*Bud*

The peduncle is short and of slender to average caliper, erect, and with an abundance of small stipitate glands and varying quantities of short, white, stiff hair, particularly on the pericarps. The color is near Strong Yellow Green, 5GY 6/8, overlaid with near Strong Yellow Green, 2.5GY 6/8, in areas exposed to the sun.

Before the calyx breaks, the bud is small in size, short, and ovoid in form.

As the calyx breaks, the color is near Moderate Red, 2.5R 4/10. The inner surface of the sepals carries a fine, woolly tomentum.

The margins of alternate sepals are lined with a fine, woolly tomentum; margins of others with several to many small stipitate glands and small slender foliaceous parts.

The outside surface of the sepals usually has several to many small stipitate glands.

The sepals sometimes are with foliaceous appendages extending to one-quarter of the sepal length.

As the first petal opens, it is small in size, short in length, ovoid, and usaully urn-shaped. The color on the outside of the petal is near Strong Purplish Red, 10RP 4/12. The color on the inside of the petal is between Strong Purplish Red, 10RP 4/12 and Moderate Red, 2.5R 4/10. The bud opens up well and is not retarded or prevented from opening by cold, hot, wet, or dry weather.

*Bloom*

The size of the bloom when fully open is small, ranging from 2½ inches to 2¾ inches. The petalage is double, with from 15 to 20 petals, arranged irregularly, plus 3 to 4 petaloids. The bloom is high-centered at first, becoming cupped to high-centered.

At first the petals are somewhat tightly cupped, with tips reflexed outward, becoming later at maturity loosely flat to cupped, with tips reflexed outward.

The outside petals of a newly opened flower are reflexed strongly outward along the apex. The outside petals of a three days open flower are reflexed outward both along the apex and along the edges.

The petals are of a medium thickness, with inside velvety and the outside satiny. The outside petals are between round and broadly obovate, usually with apex flat, but sometimes acute. The intermediate petals are round to broadly obovate, usually with apex rounded, but sometimes acute. The inside petals are between round and broadly obovate, with apex rounded. The colors may be modified by being shaded and/or washed with other colors.

The paragraphs immediately following describe color values observed in a flower newly-opened in the month of September. The plant had been grown outdoors, in Ontario, Calif.

The outer surface of the outside petal was between Strong Purplish Red, 7.5RP 5/12, and Strong Purplish Red, 10RP 4/12. The inner surface of the outside petal was near Strong Purplish Red, 10RP 4/12, blending with near Deep Purplish Pink, 7.5RP 6/12, toward the base of the petal.

The outer surface of the intermediate petal was between Strong Purplish Red, 7.5RP 5/12, and Strong Purplish Red, 10RP 4/12. The inner surface of the intermediate petal was near Deep Purplish Red, 10RP 3/10, blending with near Strong Purplish Red, 7.5RP 5/12, toward the base of the petal.

The outside surface of the inner petal was between Strong Purplish Red, 7.5RP 4/11, and Strong Purplish Red, 10RP 4/12. The inner surface of the inner petal was between Moderate Red, 2.5R 4/10, and Strong Purplish Red, 10RP 4/12.

The paragraphs immediately following describe the color values observed in a bloom which had been open for three days, outdoors, in the month of September. The plant had been grown outdoors, in Ontario, Calif.

The outer surface of the outside petal was near Strong Purplish Red, 7.5RP 5/12. The inner surface of the outside petal was near Strong Purplish Red, 10RP 4/12.

The inside petal, both on its outer surface and on its inner surface, had the same coloration as the outside petal.

The general color effect of the newly opened flower is between Moderate Red, 2.5R 4/10, and Strong Purplish Red, 10RP 4/12. The bloom after being three days open gives a general color effect which is near Strong Purplish Red 10RP 4/12.

The flower on the bush in the garden persists for from three to five days in the month of August, in the locality named. The petals drop off cleanly, and are not particularly affected by cold, hot, wet, or dry weather. Cut roses grown outdoors and kept at living-room temperatures will last from two to three days in the month of August.

*Reproductive organs*

Stamens: The stamens are average to many in number, regularly arranged about the pistils.

Filaments: The filaments are short, being 5 to 10 mm. in length, and Vivid Yellow, 2.5Y 8/12, in color. Most are with anthers.

Anthers: The anthers are small, all opening approximately at once. On both the upper and lower side the margins are near Strong Orange Yellow, 10YR 7/10, and the central area is near Pale Orange Yellow, 7.5YR 9/4.

Pollen: The pollen is moderate in quantity, and near Strong Orange Yellow, 7.5YR 7/11, in color.

Pistils: The pistils are approximately 60 in number, this being average.

Styles: The styles are uneven, short, thin caliper, and bunched. The upper half of the style is near Moderate Red, 2.5R 4/10, while the remainder is near Brilliant Greenish Yellow, 7.5Y 9/8.

Stigma: The stigma is near Pale Orange Yellow, 7.5YR 9/4.

Ovaries: The ovaries are usually all enclosed in the calyx.

Hips: Hips observed on plants grown at Ontario, Calif., were short and flattened, smooth, except for some russeting, and with thick, fleshy walls. Prior to maturity, they were near Strong Yellow Green, 2.5GY 6/8.

Sepals: The sepals fall soon. They are short to medium-length, usually straight, sometimes recurved. The color on the inside is near Brilliant Greenish Yellow, 7.5Y 9/8, while the outside is near Strong Greenish Yellow, 10Y 7/9.

Seeds: Seeds are few, 15 to 20 in number, and are usually small to medium size.

*Foliage*

The compound leaves usually comprise three to seven leaflets. They are abundant, medium size, leathery and semi-glossy. The leaflets are lanceolate, ovate to acuminate, with apex acute, base cuneate, and margin simply serrate.

The mature foliage displays on its upper surface a color between Moderate Olive Green, 5GY 4/3, and Grayish Olive Green, 5GY 3/2. The under surface is near Moderate Yellow Green, 7.5GY 5/7.

The young foliage on its upper surface is near Moderate Olive Green, 5GY 4/3, and on its under surface is near Moderate Yellow Green, 2.5GY 5/5.

The rachis is average in size, grooved on the upper side, with a few stipitate glands on the edges. The under side is smooth, except for some stipitate glands and a few prickles.

The stipules are medium-length and narrow, with short to medium-length points turning out at an angle of less than 45°.

The plant displays a more than average resistance to mildew, when compared with other varieties now in commerce and grown under comparable conditions at Ontario, Calif.

*Growth*

The plant is of bushy, spreading habit, much branched. It displays a free to vigorous growth. The canes are of medium caliper.

The main stems are near Moderate Olive Green, 7.5GY 4/4, in color. They bear several medium-length large prickles, hooked slightly downward, with medium-length, narrow base. Their color is near Brownish Orange, 5YR 5/8. There are few small prickles, and their color is the same as that of the large prickles. There are no hairs.

The branches are near Moderate Yellow Green, 5GY 5/6, in color. They bear several medium-length large prickles, hooked slightly downward, with medium-length narrow base. Their color is near Strong Yellowish Brown, 7.5YR 5/7. There are few small prickles, and their color is the same as that of the large prickles. There are no hairs.

The new shoots also are near Moderate Yellow Green, 5GY 5/6, in color. They bear few short large prickles, hooked slightly downward, with medium-length, narrow base. Their color is near Strong Yellow Green, 2.5 GY 6/8. There are few small prickles, and their color is the same as that of the large prickles. There are no hairs.

I claim:

1. The new variety of rose plant of the floribunda class, substantially as herein shown and described, manifesting in combination a plurality of the following features, namely, a notably vigorous, spreading plant, of slightly better than average resistance to mildew, having peduncles which bear a large number of short, stiff stipitate glands intermixed with some stiff white hairs, said hairs being abundant on the pericarp and where the pericarp joins the peduncle; said plant bearing flowers which typically comprise about fifteen to twenty bright red petals, many of the outer and intermediate petals of said flowers having apices with acute points; said flowers manifesting a slight fragrance, and leading to the production of hips which are typically flattened, or tomato-shape, in form.

No references cited.

ROBERT E. BAGWILL, Primary Examiner